United States Patent [19]

Goldman

[11] 4,298,800
[45] Nov. 3, 1981

[54] TOMOGRAPHIC APPARATUS AND METHOD FOR OBTAINING THREE-DIMENSIONAL INFORMATION BY RADIATION SCANNING

[75] Inventor: Arnold Goldman, Houston, Tex.

[73] Assignee: Computome Corporation, Houston, Tex.

[21] Appl. No.: 5,687

[22] Filed: Jan. 23, 1979

Related U.S. Application Data

[63] Continuation-in-part of Ser. No. 881,549, Feb. 27, 1978, abandoned, which is a continuation of Ser. No. 664,910, Mar. 8, 1976, abandoned.

[51] Int. Cl.$^3$ ............................................. G01N 23/00
[52] U.S. Cl. .................................. 250/445 T; 250/369
[58] Field of Search ............ 358/111; 250/369, 445 T, 250/416 TV, 578

[56] References Cited

U.S. PATENT DOCUMENTS

3,758,723 9/1973 Green et al. ................. 250/416 TV
3,824,337 7/1974 Sangster et al. .................... 250/578
3,881,110 4/1975 Hounsfield et al. ................ 250/360

Primary Examiner—Alfred E. Smith
Assistant Examiner—T. N. Grigsby
Attorney, Agent, or Firm—Mark C. Jacobs

[57] ABSTRACT

Apparatus for scanning a part or all of a patient by X-rays or gamma rays to obtain two or three dimensional information. The apparatus comprises a fan beam source of radiation which is moveable relative to the patient and means fixed or movably relative to the patient, but fixed relative to the source of radiation comprising a scintillation crystal or fluoroscopic screen which may be tilted at an angle, a lens system, a charge coupled device for translating the light photons received from the crystal or screen into a corresponding analog signal which can then be processed either directly by an analog computer or after conversion to digital signals, by a digital computer. The results are then exhibited by a suitable display device such as a cathode ray tube.

15 Claims, 7 Drawing Figures

TOMOGRAPHIC APPARATUS AND METHOD FOR OBTAINING THREE-DIMENSIONAL INFORMATION BY RADIATION SCANNING

REFERENCE TO RELATED APPLICATIONS

This application is a continuation-in-part of my co-pending application, Ser. No. 881,549 filed Feb. 27, 1978, now abandoned which is a continuation of my application Ser. No. 664,910 now abandoned.

BACKGROUND OF THE INVENTION

This invention relates generally to a method of an apparatus for tomographically examining an object by radiation such as X-rays or gamma rays for obtaining two or three dimensional information of the object.

Attempts have been made in the past to obtain two or three dimensional information about an object for both diagnostic and inspection purposes. In this connection it will be appreciated that when patients are involved, it is of the utmost importance to keep the exposure to X-rays and gamma rays at an absolute minimum.

Thus, the U.S. Pat. No. to Webb 3,580,997 employs a television camera to convert a radiographic image produced by a test object into video signals. This is used as an on line inspection system incorporating a go, no-go system whereby a test object or sample is compared with a standard. The patent to Siedband 3,582,651 discloses an image storage and display system intended for use with X-ray apparatus. The system has various modes such as a stop action mode, an intermittent slide mode and the like. In the diagnostic area, the patent to Corrigan, Jr. 3,679,823 reveals among other things an image intensifier used to intensify X-ray images obtained from a patient. The output of the image intensifirer is then recorded by a television camera. Much effort was expanded to improve X-ray imaging techniques prior to the work of Hounsfield who is credited with the prime mover in computer assisted tomography.

The Hounsfield patent 3,778,614, assigned to EMI, Limited, England, discloses a now commercial apparatus for examining a body such as the head of a patient with X-rays. This system of tomography has also been described in a series of three articles which appear in the Dec. 1973 issue of the BRITISH JOURNAL OF RADIOLOGY, Volume 46. The first article by Hounsfield appears on pgs. 1016 through 1022. A second paper by Ambrose appears on pgs. 1023 through 1047 and deals with the clinical application of the apparatus. A third paper by Perry and Bridges on pgs. 1048 through 1051 relates to radiation dose considerations.

The Hounsfield apparatus as described in that U.S. patent and elsewhere utilizes a pencil beam having a small cross section. He proposes to rotate the source of radiation to scan the head or object linearly to take 160 readings of X-ray transmissions per scan at the end of scan one. His system is rotated 1° for scan 2, then 1° for scan 3, etc. through 180° for a total of 28,800 readings by the detector.

The recorder consists of only one scintillation crystal and this is somewhat inefficient and hence the exposure is relatively long. Also, his detector is basically a point detector rather than an area detector. The device requires a plurality of rays to achieve the desired imaging wherein the various scans are parallel to each other whereupon the angle is changed to take each succeeding set of readings. While the system is said to be one hundred times more sensitive than conventional X-ray systems, it still requires one hundred sixty readings for each transmission and a corresponding amount of time. In any case, the exposure to the patient is between 1 and 2.5 R (roetgens).

Since the 3,778,614 patent in 1971 Hounsfield has been granted various patents, including 4,052,618 which is a division of patent 3,944,833, which itself is a division of patent 3,866,047, this application being a continuation-in-part of patent 3,778,614 which is a continuation of Ser. No. 861,538, filed in 1969.

In most tomographic instruments the X-ray source moves in one direction and the photographic film simultaneously moves in the opposite direction. The patient lies in between. If the patient's body is regarded as a series of planes parallel to the film, there is only one plane whose projected image remains stationary with respect to the film as the film moves. Hence, that plane remains sharply focused on the film and the others are blurred. To greatly simplify the procedure, the X-rays can be directed so that they pass through the patient in parallel rays as the patient (or the apparatus) is rotated in steps around a single axis. If an image were made to each step, structures in the patient's body lying in a plane perpendicular to the axis of rotation would be recorded as a single one-dimensional line. By measuring the X-ray density along that line on each image, one isolates the information from the desired plane. Thus, one can reconstruct the single two-dimensional plane and then merely stack a sequence of such planes to get a full three-dimensional picture.

The differences and the advantages of the instant system over those of Hounsfield as seen in his patent 3,778,614 and others assigned to E.P.M.I. are many in number. The system of Hounsfield, as especially espoused in his patent 3,965,357, employs a plurality of lateral scans at a succession of orbital positions so that a plane section of the body is traversed by a set of parallel beams at each of the oriented positions. The system of the instant invention does not employ or require a plurality of rotations. Here only a single rotation is to be carried out. The key to this invention is the use of the charge couple device (CCD).

In view of the program to be discussed in detail later on in this application, it is believed that the program coupled with the advantages of using the CCD will render the instant system better and cheaper than any currently on the market or known to be under development.

The properties of the CCD that make it beneficial for incorporation into an X-ray system are the facts that CCDs are relatively low in cost and are seen to be extremely accurate in measuring the light falling upon them.

A further advantage to the use of the CCD in the X-ray system of this invention is the fact that the rapid cycling due to the presence of a shift register function allows the detected linear sequence of light measurements, which are in analog form based upon the number of electron pairs per element in the CCD, to be read out at high speed while the next measurement on the patient is being made. This ability contributes to the lack of necessity of the back and forth repetitive motion required in other types of X-ray apparatus tomographic systems.

Further, since the CCD is capable of operating at very low noise levels, especially when cooled, the signal that comes in can be detected even though it has not been amplified by any preceding stages. Whereas, however, in all other known prior art systems the input signal must undergo amplification. This benefit is extremely appealing to the X-ray practitioner since prior art computer tomographic apparatuses do not enjoy such a benefit.

In the device of this invention the only modification of the input signal that takes place is the focusing of same by a lens or fiber optic means. There is no amplification as that term is known by the CCD of the light signal. The CCD which is an electro-optical device creates electron pairs which can then be transmitted along a path on the chip to a pre-amplification stage. The outgoing electrical analog signal is converted into a digital signal for use with the computer program.

It is accordingly an object of the present invention to provide a method of and apparatus for practicing tomography which is substantially more efficient in time than other methods and is more accurate than prior art units.

A further object of the present invention is to provide a method of and an apparatus of the type discussed which permits one to obtain three dimensional information by radiation applied to a patient or other object in the order of two seconds or less, hence minimizing the likelihood of unsatisfactory results due to patient's movement, or breath holding inability.

Still another object of the present invention is to provide a system of the type referred to which utilizes an image sensor which inherently has greater accuracy than the devices utilized by the prior art.

Yet another object is to provide a means wherein the radiation is distributed more uniformly in that a 360° revolution may be employed.

A still further object is to provide a tomographic device which employs an area image sensor or detector, rather than a single ray detector.

A yet further object is to provide a tomographic device which will give sufficient information for diagnostic purposes but with reduced exposure of the patient to radiation.

Other objects of the invention will in part be obvious and will in part appear hereinafter.

SUMMARY OF THE INVENTION

In accordance with the present invention there is provided an apparatus for obtaining a two- or three-dimensional image of all or part of a patient, man or beast. The object may, for example, consist of some organ of a patient such as the brain, or the entire body of a mammal. The object may be alive, as would be the normal situation, or dead if detailed analysis were needed for use specific medical or legal reason. This analysis is effected by means of X-rays. It will be understood that the term X-rays includes other hard radiation such as gamma rays which may be generated by a suitable radioactive isotope or radionuclide such as, for example, $Am^{241}$ of $I^{125}$.

Thus, there is provided a generator of hard radiation or X-rays. Fluoroscopic means, such as a screen or scintillation crystal, is provided following the object for transforming the X-ray photons into light photons without amplifying their magnitude. That is, the correlation between the X-ray photons and the light photons is direct, the exact amount of light photons being related only to the chemical nature of the fluoroscopic means utilized. No attempt is made to amplify or intensify the light photons as this action tends to introduce noise and other undesirable characteristics into the light image being formed by the fluoroscopic means. Preferably the fluoroscopic screen is disposed at an angle with respect to the axis of the X-rays to increase the absorption of X-rays. As used herein, the term fluoroscopic screen is meant to include a scintillation crystal.

The light photons liberated in the screen are then caused to impinge upon an electronic charge-coupled device or area image sensor. This will be subsequently explained. Such a charge-coupled device has the advantage of great efficiency and great accuracy because the spatial relationship of the output signal is determined by the construction of the image sensing device.

A lens system may be disposed between the screen and the device for imaging the light photons on the device. This may, for example, consist of a cylindrical lens such as a rod and a large aperture spherical lens. Here again no attempt is made to intensify the light photons.

Means are provided for causing a relative rotation between (a) the object to be scanned and (b) the generator, screen, lens system and charge coupled device. This last is often referred to as C.C.D.

The resulting analog signal is then processed in a known manner, as will be subsequently explained, and the thus obtained information is displayed in any suitable manner, for example, by a cathode ray tube or else by a computer print out. If a cathode ray tube is utilized, a suitable camera, still or motion picture, may be attached thereto to obtain at any instant photographs of the image on the cathode ray tube.

Charge-coupled devices such as an image sensor or area image sensor are well known in the art. In this connection reference is made to a survey article which appears in the Feb. 1974 issue of Scientific American, pgs. 22–31, by G. F. Amelio. The device was initially described by Boyle et al in the Bell Systems Technical Journal, Apr. 1970, pgs. 587–600. Imaging devices specifically have been described by Barbe in Proceedings of the IEEE, Volume 63, No. 1, Jan. 1975, pgs. 38–66. The application of these devices to infrared detection and imaging is described in the same issue of the Proceedings of the IEEE, by Steckl et al, beginning on pg. 67.

Charge-coupled devices are presently available from Fairchild Semiconductor, Mountain View, CA, among others. In this connection reference is particularly made to Models CCD 101, CCD 110 and CCD 121 for which data sheets are available from Fairchild.

In this connection reference is made to a series of patents, all assigned to Fairchild Camera and Instrument Corporation. Among these is a patent to Kim 3,728,590. This patent relates to details of construction of such CCDs. The patent to Dyck et al 3,717,770 deals with a binary array for such devices having staggered chips. The Early patent 3,806,772 discloses a charge-coupled distributed amplifier. The Amelio and Salsbury patent 3,838,409 has to do with the construction of such devices utilizing MOS or bipolar transistors having S $O_2$-S interfaces. The Amelio patent 3,865,067 reveals a method of preventing saturation of a charge-coupled device by draining off excessive carries from a potential well. The Amelio-Kim et al patent 3,853,634 deals with the method of forming a two-phase charge-coupled device rather than a three-phase device. The patent to Sander 3,859,518 discloses a charge-coupled device for detecting changes in ambient light conditions. The development of new CCDs and uses for them are continually being made known.

Basically, a charge-coupled device is a semiconductor device wherein the mobile electric charges stored within a storage element are transferred to an adjacent storage element. This is effected by varying external voltages applied to the device either in a two- or three-phase. Thus, basically a potential well is raised or lowered for the purpose of discharging or storing electric charges represented by charge carriers. The device is characterized by its extreme accuracy in locating the precise area whereupon the light photons were received.

The CCDs contain a large plurality of image sensor elements separated by diffused channel stops and covered by a silicon gate. For instance, CCD 121 is a 1728 element linear image sensor wherein all 1728 are in a row. In addition, this integrated circuit device also includes two two-phase analog shift registers, preamplification and amplification (electronic, not light) stages. This device is constructed to present sequential reading of the 1728 imaging elements.

Other CCD chips serve similar and different functions, as for example CCD 311 which is a 130/260 bit analog shift register device. Still others, such as CCD 201, are area image sensors, as opposed to linear image sensors. CCD 121 is a low noise sensor device of 100×100 photoelements.

The basic functions of a CCD image sensor are: (1) to sense and store photon-generated charge in an array of deplection regions or potential wells that are formed by an MOS-type capacitor; (2) to transfer the signal from each element in the photosensing array in the form of a pocket of charge which is moved or clocked through a series of potential wells to a detector-preamplifier. Because the device is most conveniently illuminated at the top of the silicon substrate or front-side, the photogate electrode consists of a film of polycrystalline silicon that is thin enough to transmit visible radiation. The individual photoelements are defined or electrically isolated by a channel stop. This may be formed in the case of an n-channel device by a narrow p-type region in the silicon substrate. Charge packets generated by light under the photogate are transferred in parallel to the adjacent CCD shift register, which is opaque. The packets are then stepped or clocked to the detector-amplifier. In the case of an area sensor, which consists of columns of photoelements, this design has been called "interline transfer". It is understood that it is also apparent that the interline transfer register requires approximately half the silicon area in the area-photosensor array to be opaque; the photo-element charge capacity is therefore half that of the frame-transfer design for the same photosensor area. Because of the low noise properties of the device, this does not limit the dynamic range. Further information of the functional design of CCD chips may be had from a paper published prior to 1976 by A. L. Solomon of Fairchild, entitled "Parallel-Transfer-Register Charge-coupled Imaging Devices". It is recognized that in a linear array there is no interline transfer; therefore no loss of sensitive area.

While area image sensors are employable in this invention, I have found that in the current state of the art, the linear device that is 1×1728 elements is preferred because it is the longest device available in terms of physical size. The larger the CCD, the less the minification factor in focusing the light photons from the crystal or screen on the CCD.

The linear CCD still gives rise to an area end image since each linear projection is based upon multiple beams which are sorted out by the computer during the course of the reconstruction.

The novel features that are considered characteristic of this invention are set forth with particularity in the appended claims. The invention itself, however, both as to its organization and method of operation, as well as additional objects and advantages thereof, will best be understood from the following description when read in connection with the accompanying drawings.

BRIEF DESCRIPTION OF THE DRAWINGS

It is seen that all of the above figure descriptions and the discussion below assume that the patient is not in a supine position, but in a vertical one, i.e., standing or sitting. When the patient is viewed in a reclining (lying down) position, then FIG. 1 is an end view, FIG. 2 is a top view and FIG. 4 is an end view. Present techniques for apparatus construction permit units to be built such that the patient can be horizontal or vertical as suits the doctor's wishes.

FIG. 5 is a schematic diagram of apparatus in accordance with this invention wherein a plurality of image detectors are employed; while

DESCRIPTION OF THE PREFERRED EMBODIMENT

Figure 1:
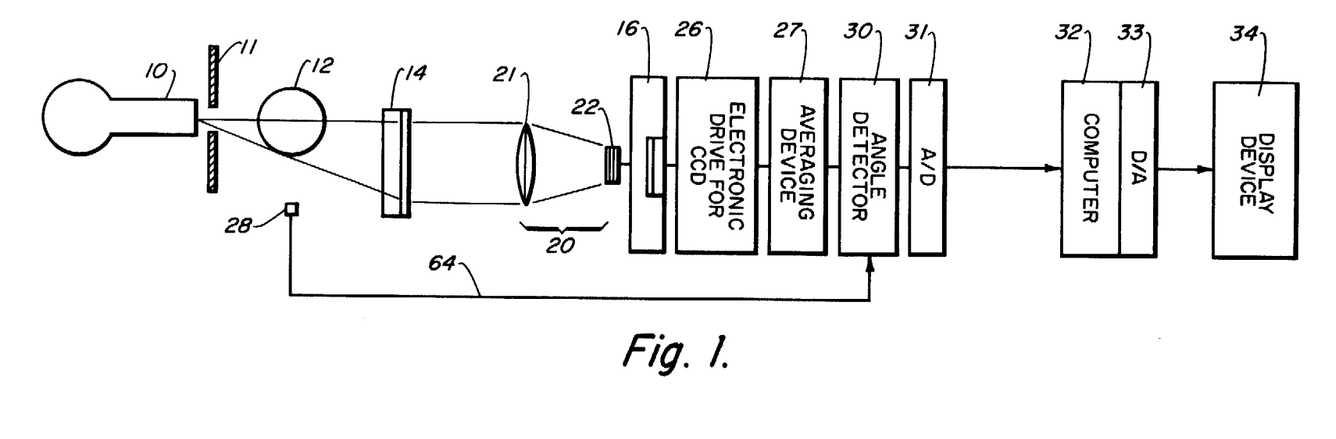
FIG. 1 is a schematic top plan view of an X-ray scanning apparatus in accordance with the present invention.
Figure 2:
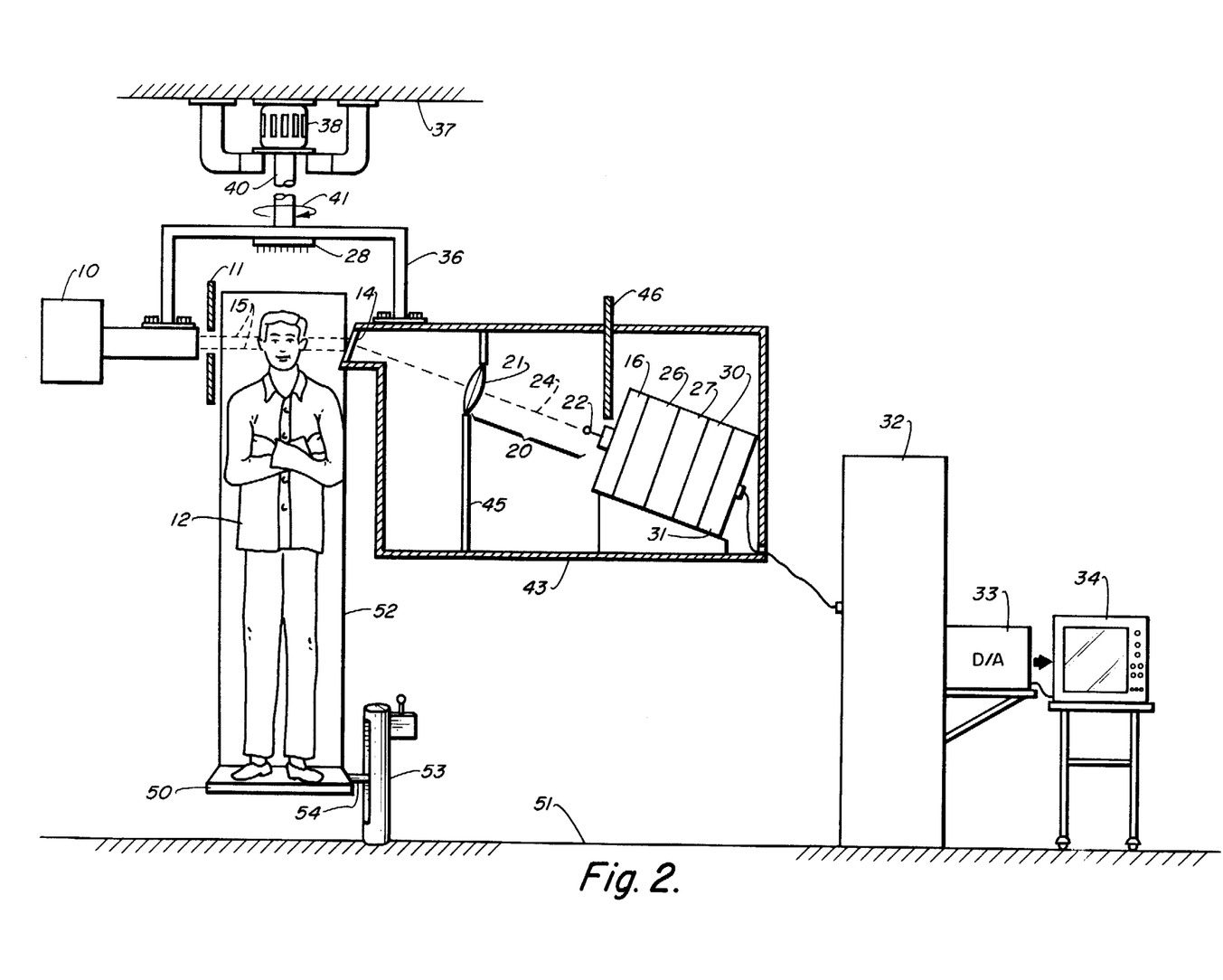
FIG. 2 is a detailed side elevational view of the apparatus of FIG. 1 including the mechanism for rotating the X-ray beam about the patient and for moving the patient with respect to the radiation beam.

Referring now to the drawings and particularly to FIGS. 1 and 2, there is illustrated a schematic top plan and side elevational view of apparatus embodying the present invention. The apparatus includes a source or generator 10 for generating hard radiation such as X-rays or gamma rays. As explained hereinbefore, the term X-rays or X-ray sources is meant to include gamma rays or other hard, that is penetrating, radiation or a gamma ray source such as a radioactive or radionuclide source.

In case an X-ray tube is used it may be operated at about 110 KVp (kilovolts peak) at 400 ma (milliamperes). The X-ray generator may be one obtainable from Picker e.g. GX600. The tube itself may be one manufactured by Machlett having heat unit capacity of 300,000 which corresponds to the anode capacity.

Basically the X-ray source 10 is adapted to generate a narrow fan-like beam rather than a "pencil" beam as employed in many tomographic systems. Hence the tube may be provided with a suitable slit 11 encompassing half or all of the width of the object being examined and, if necessary, with a collimator. This narrow fanscopic screen as it has less absorption capability and less density. It has been found, however, that by tilting the screen relative to the X-ray tube that the effective thickness is increased, thereby increasing its capacity to absorb X-rays.

Figure 3:
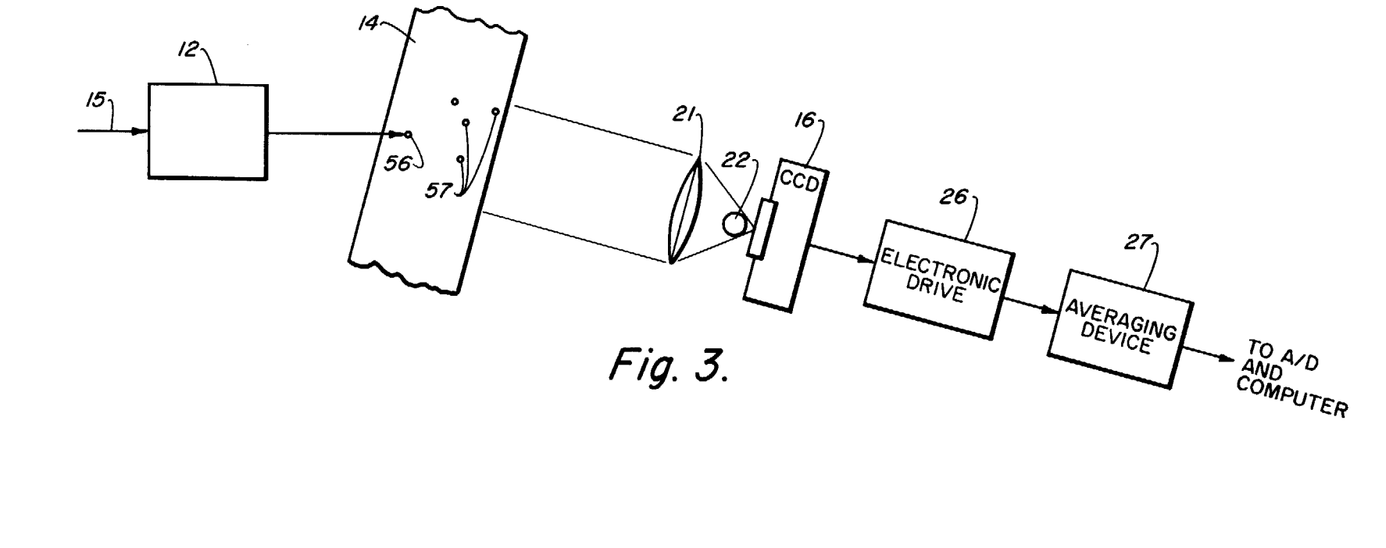
FIG. 3 is a schematic side elevational view to illustrate how the X-rays having passed an object are converted into light photons, focused on a charge coupled device and subsequently amplified and averaged.

The light photons now impinge upon the lenses 21 and 22 which are optical lenses, to focus information on the CCD. These lenses 21, 22 form the light from a large area, namely the screen down to a small area, namely the CCD 16. The light photons give rise to an electrical signal which may be first processed by the electronic drive 26 which functions to supply proper voltages for the function of the CCD and which can receive the output signal from the CCD if processing is desired before transmission to the averaging device.

Averaging circuit or averaging device 27, which is entirely optional and can be omitted entirely, produces an output signal having an amplitude proportional to the average value of the detected signal. The term "average value" means the value of the detected signal averaged by circuit 27 over a time interval determined by the circuit time constant.

The use of an averaging circuit allows the operator to employ less signal sampling for processing purposes. Averaging circuits constituting capacitor resistance feedback loop amplifiers may be employed for this purpose. Such an amplifier is available in the marketplace.

Indeed, averaging circuits are not new; they have been disclosed at least as early as 1975 in U.S. Pat. No. 3,903,512.

Figure 6:
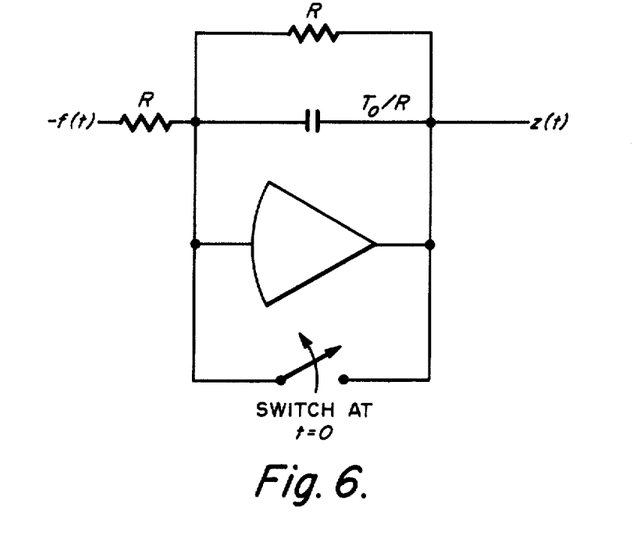
FIG. 6 is a circuit diagram employable herein.
Figure 7:
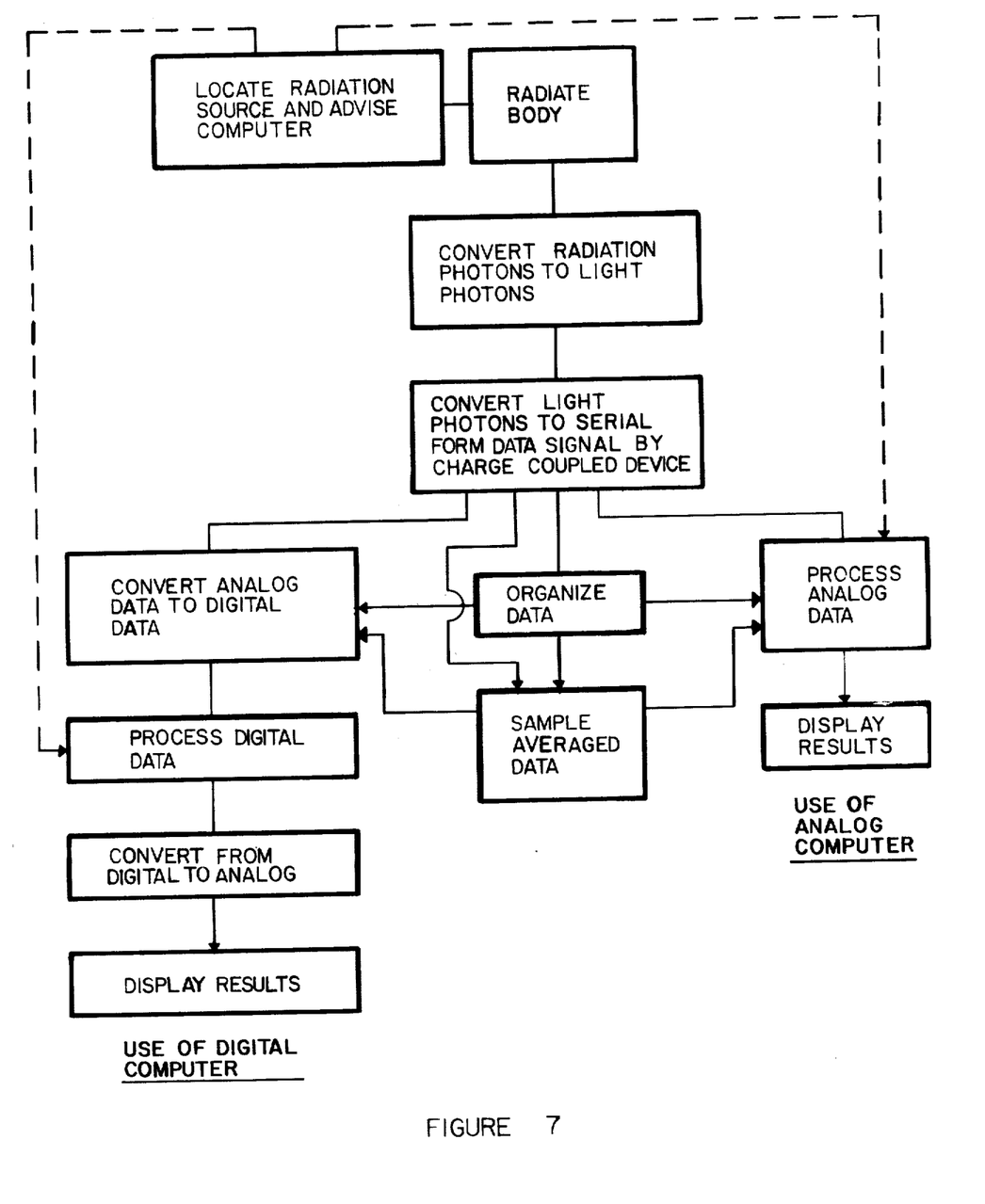
FIG. 7 is a flow diagram of the process steps.

A specific averaging circuit that may be employed herein is disclosed in a paper entitled *Continuous Data Analysis With Analog Computers Using Statistical and Regression Techniques* by Arthur I. Rubin of the Princeton Univ. Center, dated Dec. 20th, 1960, at P. 96 and reproduced here as FIG. 6.

The average value obtained is exponentially weighted past (that is, the nearer in time to the instant of averaging, the greater the weight given to the value.

Thus it may be assumed that each X-ray photon absorbed by the screen 14 generates in turn M light photons. The number of X-ray photons captured or absorbed by the screen 14 is a function of the screen thickness, and of the angle of tilt and the absorption co-efficient of the screen material. This may be on the order of 50-80% or more of the incoming X-ray photons. The number M may be assumed to be about 3000-8000. The number of these to form one electron-hole pair in the charge coupled device may be assumed to be about 4-8.

The optical system 21, 22 in turn must capture or focus enough of the light photons on the screen of the charge coupled device 16 to avoid loss of information. This in turn requires the properties of the lens system previously discussed.

It will be understood that the light impinging on the charge coupled device 16 will in turn create electron-hole pairs. The number K of such electron-hole pairs is a function of the intensity of the incident light and its wavelength.

The digital information impressed upon the computer 32 may be processed by using polar or rectangular coordinates. Specifically, the desired information contained in the digital signals may be recovered by Fourier methods, convolutional methods, matrix inversion or iterative methods. While references to some of these methods are known to the art, they will be discussed in more detail infra.

Figure 4:
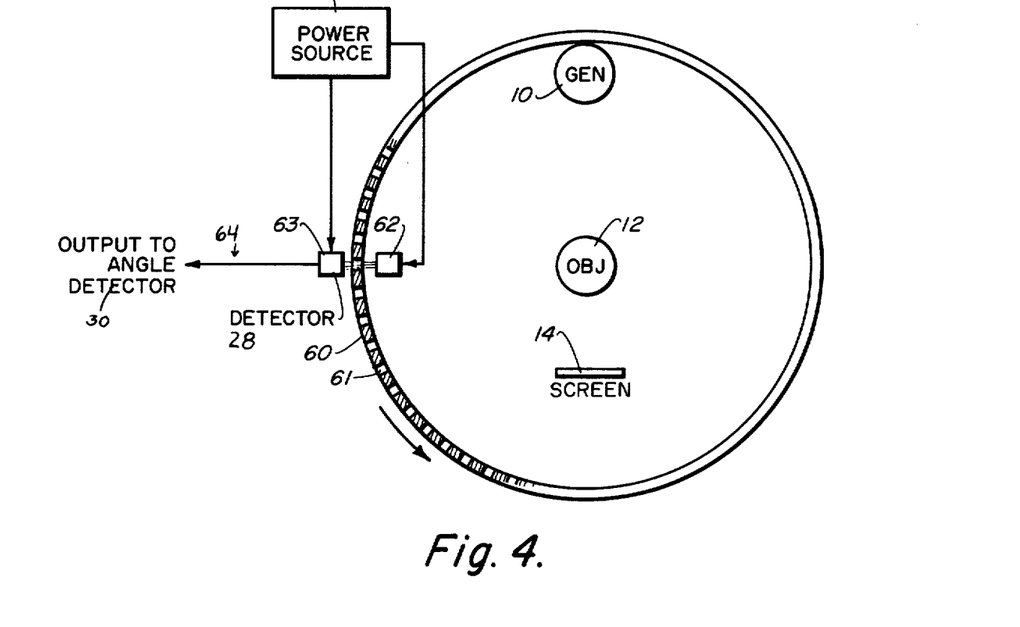
FIG. 4 is a schematic top plan view illustrating by way of example how the angular position of the scanning X-ray beam with respect to the object may be measured to supply the angular information to the computer.

Reference is now made to FIG. 4 which illustrates by way of example an angular position detector of the type referred to in FIGS. 1 and 2, that is the detector 28. FIG. 4 again shows the X-ray generator 10, object 12 and screen 14. Movable with the generator 10 is an annular perforated ring 60, a ring having a plurality of apertures or holes 61. These apertures are illuminated by a stationary light source 62 such as a light emitting diode. Such a circular disc has a plurality of spaced apart holes at regular intervals, such as 1° or ½° apart around the periphery. As is seen in FIG. 4, the ring is fixed relative to the tube, which is capable of rotation as previously discussed. The light source, such as an LED 62, and the detector 63, often a light sensitive silicon diode, are fixed. The disc with the X-ray tube moves relative to the light source. At an arbitrary point designated (1) the apertures are numbered in sequence forwardly. As the ring 60 rotates relative to the light, light flashes through the apertures and the detector 63 receives the light signals and the angle detector 30, a counter, counts them and advises the computer of the angle or location of the X-ray tube in degrees which correspond to the number of light impulses counted.

When the light from the light emitting diode 62 passes through one of the apertures 61, it will fall on light detector 63 which will generate an output signal on an output lead 63 which can be impressed on the angle detector 30 of the FIGS. 1 and 2.

A power source 65 powers both the light source 62 and detector 63. Thus, detector 28 would be comprised of components 60,61,62,63 and 65. Counters capable of receiving output signal 64 and advising the computer of the various angles per signal 67 in the proper time sequence are made by Kessler-Ellis Products, Atlantic Highlands, New Jersey, (SC-116 Miniature), among others.

Other types of angle detectors or X-ray tube location determinators may be employed such as potentiometers that give a slight change in electrical potential at each different degree or partial degree interval which change can be monitored for the same purpose can be employed. Such potentiometers and counters and readily available in the marketplace.

It is also within the scope of the invention to employ a plurality of area image detectors (CCDs) in combination for certain special circumstances, such as improving spatial resolution.

The use of such a plurality of detectors makes the use of a less sophisticated lens system possible, since the information from the scintillation crystal need not be geometrically reduced as much, if a plurality of CCDs are used. However, the complexity of the electronics involved will probably lead to higher costs since a multiplexing system or some other means of combining outputs into the computer is needed. Money can be saved however by using a unitary power supply and/or drive board.

Figure 5:
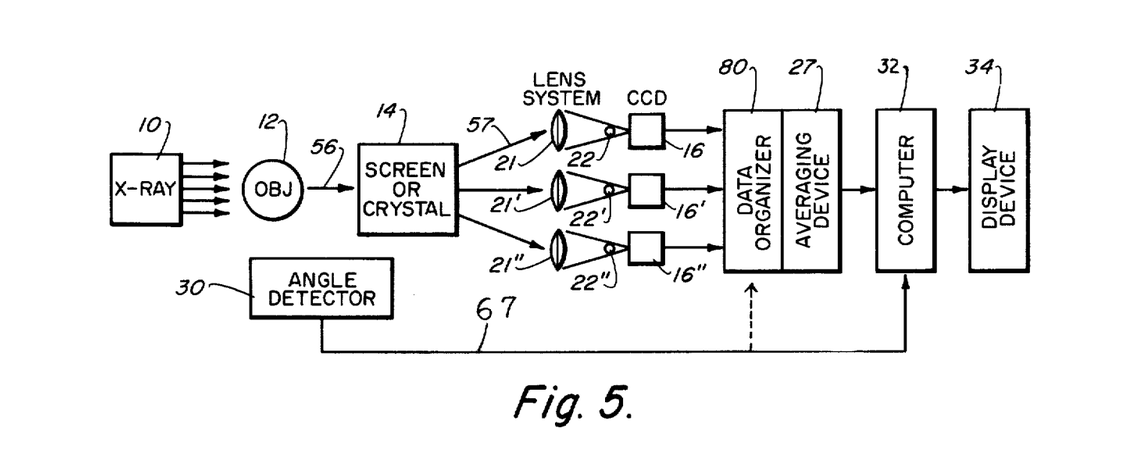

Thus reference is made to FIG. 5. Since the mode of operation is similar to that of FIG. 3, details prior to the impingement on the plurality of lenses 21-22,21'-22', and 21"-22" need not be discussed. Subsequent to the impingement of the X-rays upon screen 14, the light photons 57 are focussed by the three lens systems on to the three CCDS 16,16',16". An electrical signal from each CCD corresponding to the composite of information received by the many elements of each CCD is delivered to a data organizing station or data organizer 80.

gives the largest change in each element for an equal number of photons.

The device 16 includes an electronic drive 26 for periodically gating out the information contained therein. The analog signal developed by the device 16 and its electronic drive 26 is optionally passed through an averaging device 27. The purpose of the averaging device is to reduce the data output rate of the sampled information which must be subsequently processed by an analog or digital computer.

There is further provided a detector 28, the purpose of which is to detect the angular position of the X-ray generator 10 with respect to a fixed point. This angular information obtained from the detector 28 is then impressed upon an angle detector 30 from where it is sent to the computer to be used for identification of the analog signal obtained from the device 16 or the averaging device 27.

In case the signal obtained from the charge coupled device 16 is to be processed by a digital computer, an analog-to-digital converter 31 will have to be provided. The thus obtained digital signal is then processed by a digital computer 32 in a manner which will subsequently be described. The digital signal from the computer 32 is then reconverted by a digital-to-analog converter 33 into an analog signal which can subsequently be displayed by the display device 34. The display 34 may, for example, consist of a color television tube or else a cathode ray tube with or without a camera. It is also feasible to display the information obtained from the computer 32 by a line printer. A suitable camera may be interconnected to the display device for permanently recording the displayed image at any desired instant.

It should be distinctly understood that instead of using a digital computer 32, an analog computer may be used. In that case, of course, the analog-to-digital converter 31 and the digital-to-analog converter 33 may be omitted. How the digital computer is utilized to process the information will be subsequently explained. Computer input data is in serial form.

Referring now particularly to FIG. 2, the physical arrangement will be explained which is utilized for causing a relative motion between the object 12 and the X-ray beam 15. In general, it will be preferred to rotate the equipment about the object, particularly if the object is a human patient. It should also be understood that the rotation need not be a circular rotation, but instead could be some other form of rotation. In many instances a closed loop is traced about the object 12 by the X-ray beam. It is to be noted, however, that the motion to be employed is not transverse and circular sequential motion as employed by Hounsfield of EMI, ALTA and Ohio Nuclear in their tomographic systems.

As indicated above, how this is effected is illustrated by way of example in FIG. 2. Here the X-ray tube or source 10 is mounted on one arm of a C-shaped bracket 36 which may, for example, be rotatably secured to a fixed platform 37 such, for example, as the ceiling of a room. A drive motor 38 will rotate the bracket 36 through a shaft 40, for example, in the direction of the arrow 41.

The other arm of the bracket 36 will rotate at the same rate as a housing 43 which houses, as shown, the fluoroscopic screen 14, lens system 20, charge coupled device 16 with its electronic drive 26, as well as the optional averaging device 27, angle detector 30 and analog-to-digital converter 31. Each of these has been described at least in brief and will be described in more detail below.

The lens 21 may be held in a suitable holder 45 secured to the housing 43 and designed to hold the lens 21 normal with respect to the axis 24. A shield 46 is disposed in the housing 43 for shielding the charge coupled device 16 from X-rays and undesired light rays.

As shown in FIG. 2, the patient or object 12 is disposed upright on a platform 50 which in turn may be secured to a fixed portion of the building such as the floor. It should be specifically noted that while the patient has been shown in FIGS. 1 and 2 to be standing upright, he could also be disposed in a horizontal position on a suitable table. In that case, of course, FIG. 1 would not be a top plan view, but a side elevational view, while FIG. 2 would not be a side elevational view, but a top plan view.

The image on screen 14 may be way of example by 12 centimeters wide. However, a single fan-like X-ray beam may be divided by the device 16 into 80 or more separate readings so that the screen areas sampled are basically only 1.5 millimeters wide. Furthermore, the height of the image on the screen may be way of example be 3 millimeters high.

It is usually desirable to take more than a single tomograph, that is more than a single slice through the object 12. To this end the patient may be disposed on a platform or support 52 which may be raised or lowered, preferably in predetermined increments, for example, by the rotation of a screw 53 extending through horizontal arms 54 secured to the support 52 of the patient. In this manner the object or patient may be moved say upwards as shown in FIG. 2 in predetermined increments to scan predetermined horizontal slices of the object. It will be understood that the mechanical arrangement, including the screw 53, is only shown by way of example. Alternatively, the person 12 could be placed on a rotating platform that moved in clickstop increments.

It is seen that a single scan, that is a single revolution of the X-ray generator 10 about the object 12, may take on the order of two seconds or less. For reasons well known to practitioners of radiology, it is desirable to reduce the time the patient is exposed to X-rays.

Referring now to FIG. 3, it is illustrated in more detail how the X-rays are converted into light photons by the fluoroscopic screen 14. Thus, the X-ray beam 15 passes through the object 12 and an X-ray photon 56 is absorbed by the fluoroscopic screen 14. This in turn generates a plurality of light photons 57. Each X-ray photon possesses a large amount of energy and is capable of generating a large plurality of light photons. It is seen that the fluorescent screen or scintillation crystal 14 employed herein is not an amplifier. It is a transducer that gives off light photons proportional to the X-ray signal tht impinges upon it; the X-ray signal being equal to the sum of the X-ray photons. The efficiency of the screen 14 is up to 90±% in its ability to X-ray photons. Of the about 90± of the X-ray signal absorbed about 30±% of the energy is transformed into light photon and emitted. While each light photon has less energy than an individual X-ray photon, there are many more light photons 57 available. Part 14 does not amplify or intensify the signal.

Mention should be made of the angularity of the screen 14. Since a scintillation crystal is of high density and has high absorption capability, tilting is optional. The tilting is a more preferred procedure with a fluoroscopic screen as it has less absorption capability and less density. It has been found, however, that by tilting the screen relative to the X-ray tube that the effective thickness is increased, thereby increasing its capacity to absorb X-rays.

The light photons now impinge upon the lenses 21 and 22 which are optical lenses, to focus information on the CCD. These lenses 21, 22 form the light from a large area, namely the screen down to a small area, namely the CCD 16. The light photons give rise to an electrical signal which may be first processed by the electronic drive 26 which functions to supply proper voltages for the function of the CCD and which can receive the output signal from the CCD if processing is desired before transmission to the averaging device.

Averaging circuit or averaging device 27, which is entirely optional and can be omitted entirely, produces an output signal having an amplitude proportional to the average value of the detected signal. The term "average value" means the value of the detected signal averaged by circuit 27 over a time interval determined by the circuit time constant.

The use of an averaging circuit allows the operator to employ less signal sampling for processing purposes. Averaging circuits constituting capacitor resistance feedback loop amplifiers may be employed for this purpose. Such an amplifier is available in the marketplace.

Indeed, averaging circuits are not new; they have been disclosed at least as early as 1975 in U.S. Pat. No.3,903,512.

A specific averaging circuit that may be employed herein is disclosed in a paper entitled *Continuous Data Analysis With Analog Computers Using Statistical and Regression Techniques* by Arthur I. Rubin of the Princeton Univ. Center, dated Dec. 20th, 1960, at P. 96 and reproduced here as FIG. 6.

The average value obtained is exponentially weighted past (that is, the nearer in time to the instant of averaging, the greater the weight given to the value.

Thus it may be assumed that each X-ray photon absorbed by the screen 14 generates in turn M light photons. The number of X-ray photons captured or absorbed by the screen 14 is a function of the screen thickness, and of the angle of tilt and the absorption coefficient of the screen material. This may be on the order of 50-80% or more of the incoming X-ray photons. The number M may be assumed to be about 3000-8000. The number of these to form one electron-hole pair in the charge coupled device may be assumed to be about 4-8.

The optical system 21, 22 in turn must capture or focus enough of the light photons on the screen of the charge coupled device 16 to avoid loss of information. This in turn requires the properties of the lens system previously discussed.

It will be understood that the light impinging on the charge coupled device 16 will in turn create electron-hole pairs. The number K of such electron-hole pairs is a function of the intensity of the incident light and its wavelength.

The digital information impressed upon the computer 32 may be processed by using polar or rectangular coordinates. Specifically, the desired information contained in the digital signals may be recovered by Fourier methods, convolutional methods, matrix inversion or iterative methods. While references to some of these methods are known to the art, they will be discussed in more detail infra.

Reference is now made to FIG. 4 which illustrates by way of example an angular position detector of the type referred to in FIGS. 1 and 2, that is the detector 28. FIG. 4 again shows the X-ray generator 10, object 12 and screen 14. Movable with the generator 10 is an annular perforated ring 60, a ring having a plurality of apertures or holes 61. These apertures are illuminated by a stationary light source 62 such as a light emitting diode. Such a circular disc has a plurality of spaced apart holes at regular intervals, such as 1° or ½° apart around the periphery. As is seen in FIG. 4, the ring is fixed relative to the tube, which is capable of rotation as previously discussed. The light source, such as an LED 62, and the detector 63, often a light sensitive silicon diode, are fixed. The disc with the X-ray tube moves relative to the light source. At an arbitrary point designated (1) the apertures are numbered in sequence forwardly. As the ring 60 rotates relative to the light, light flashes through the apertures and the detector 63 receives the light signals and the angle detector 30, a counter, counts them and advises the computer of the angle or location of the X-ray tube in degrees which correspond to the number of light impulses counted.

When the light from the light emitting diode 62 passes through one of the apertures 61, it will fall on light detector 63 which will generate an output signal on an output lead 63 which can be impressed on the angle detector 30 of the FIGS. 1 and 2.

A power source 65 powers both the light source 62 and detector 63. Thus, detector 28 would be comprised of components 60,61,62,63 and 65. Counters capable of receiving output signal 64 and advising the computer of the various angles per signal 67 in the proper time sequence are made by Kessler-Ellis Products, Atlantic Highlands, New Jersey, (SC-116 Miniature), among others.

Other types of angle detectors or X-ray tube location determinators may be employed such as potentiometers that give a slight change in electrical potential at each different degree or partial degree interval which change can be monitored for the same purpose can be employed. Such potentiometers and counters and readily available in the marketplace.

It is also within the scope of the invention to employ a plurality of area image detectors (CCDs) in combination for certain special circumstances, such as improving spatial resolution.

The use of such a plurality of detectors makes the use of a less sophisticated lens system possible, since the information from the scintillation crystal need not be geometrically reduced as much, if a plurality of CCDs are used.However, the complexity of the electronics involved will probably lead to higher costs since a multiplexing system or some other means of combining outputs into the computer is needed. Money can be saved however by using a unitary power supply and/or drive board.

Thus reference is made to FIG. 5. Since the mode of operation is similar to that of FIG. 3, details prior to the impingement on the plurality of lenses 21-22,21'-22', and 21"-22" need not be discussed. Subsequent to the impingement of the X-rays upon screen 14, the light photons 57 are focussed by the three lens systems on to the three CCDS 16,16',16". An electrical signal from each CCD corresponding to the composite of information received by the many elements of each CCD is delivered to a data organizing station or data organizer 80.

Suffice it to say that while a specific box for the electronic drive for the CCDs is not shown, it is to be inferred. As is known, the electronic drive for the CCDs comprises a power supply and appropriate circuitry, as particularly specified by the manufacturer of the CCD in question in the user's manual.

Data organizer 80 codifies and organizes the data sent either directly to the computer, or to the computer via the averager 27 previously discussed. The data organizer acts as a sequencer to indicate to the computer the relative location in space for the continuing supply of data emanating from the CCDs for the computer to use in making its reconstruction.

The data organizer 80 often forms a part of original equipment manufacturer's computer hardware package. Such a device 80 comprises a direct access memory. The organizer seeks an appropriate memory address for the successive digital words. It is basically two storage registers for each channel with the word to be addressed in one and the address in the other. The address corresponds to the location in space of the data information.

In addition to being available as part of an original equipment manufacturer's computer package, one can purchase a data organizer as a separate unit. Thus Modcomp Corp. of Fort Lauderdale, Florida offers its Modex line having direct memory access with at least A/D conversion built in for up to 16 channels.

The data entering the component is given an address and the data is then put directly into the core without it having to be processed by the C.P.U. Thus data can be handled quite rapidly without backlogging. Obviously it is seen, that each channel could be allocated a separate CCD in a set-up employing multiple detectors.

The signals are as is seen in FIG. fed from the data organizer 80 to the optional averaging device 27 as previously discussed, and then to the computer 31 from which the information is fed to display 34, as per infra. The location of the tube as determined by angle detector 30 based on input 64 from detector 28 is fed as 67 either directly to computer 31 or optionally to organizer 80 if 80 is a discrete component & not built into computer 34.

It is seen that the reconstruction of a three-dimensional picture is based on the technique of reconstructing a two-dimensional picture, or cross section, from its one-dimensional projections. The application of any mathematical mode of reconstruction to a finte amount of data yields only a good estimate of the actual structure being imaged. The accuracy is obviously dependent upon the nature of the input data.

To verify the accuracy of a technique, one applies it to a known structure and compares the actual structure with the mathematical reconstruction by calculating the pluralty of 1D projections at various angles, from any two-dimensional image of the device in question.

Several means have been devised for gathering the multiplicity of one-dimensional projections of the test picture. A basic technique includes the recording on film of the projection of the test picture as a blurred set of streaks with the density of each streak corresponding to the integrated density of the picture to that particular angle from which that particular images as made. By adding up photographically all of the streak pictures, one can achieve a summation reconstruction of the picture. Unfortunately the accuracy of this summation technique has been found to be lacking. Accordingly an algebraic method known as Algebraic Reconstruction Technique (ART) is utilized with a digital computer for obtaining quantitative accuracy for three-dimensional information. Since this ART algorithm (computer program) is known to the art, it need not be amplified upon further other than to say that when with the varying of the mode of expression of the device of this invention from the general tomographic devices as evidenced by Hounsfield, still the algorithm is applicable for obtaining the desired information in the device of this invention. The ART algorithm is described in brief in SCIENTIFIC AMERICAN, Oct. 1975 at page 56 et seq.

Another article that discusses an algorithm applicable for use with the instant invention is found in PHYS MED BIOL 1974, vol. 19, #4 at pages 511–522 pertaining to a computerized image reconstruction method by Zho et al. This article deals with Superposition with Compensation. Others refer to this technique as convolution and back projection. These articles are incorporated herein by reference.

Computer programs for the reconstruction of fan beam scans and the like are well known in the art. In this connection reference is made to a paper by Lily Wang et al., supported in part by ERDA under Contract AT (04-01) GEN-12 and has been published as Paper No. WB 6-1. This paper proposes to use the convolution method and linear superposition for the fan beam approach. The method has been specifically designed for the Hounsfield apparatus previously discussed and is equally applicable for the reconstruction required herein.

Reference is also made to a recent article in the Scientific American by Gordon et al. which appears in the Oct. 1975 issue, pages 56 through 68. This paper refers to a summation method where the densities of all rays are added. While perhaps not the best technique mathematically, the reconstruction calculations can be carried out in this way as well.

Finally, reference is made to the June 1974 issue of Nuclear Science (IEEE Transactions), Vol. NS-21, No. 3. The entire issue is devoted to the computational aspects of three dimensional image reconstruction. These papers again discuss convolution techniques and Fourier transforms as well as a linear algebra; that is a set of simultaneous equations which can be solved. The Fourier reconstruction of a head section is specifically discussed in a paper beginning on page 21 by Shepp et al. The paper by Gordon, beginning on page 78, discusses algebraic reconstruction techniques which have been specifically devised for the Hounsfield apparatus and may be employed with this invention. Reference is particularly made to page 90 of the paper which summarizes four major classes of reconstruction algorithms.

It will, therefore, be evident that many computer programs are presently available for processing the analog information obtained from the apparatus of the present invention and generally for performing tomography. Any of these can be readily applied to create the reconstructions necessary from the data made available from the devices of this invention. The invention herein lies in the apparatus to give rise to meaningful data, not to any computer, computer program or algorithm which could utilize this data.

It is seen that since the instant system requires only a few seconds for data acquisition time, that breath holding for patients is made easier. Due to the short required time, better dynamic studies, physiologic movements, etc. are possible.

In the discussion of FIG. 2 it was indicated that a closed loop patter of 360° radiation is used in many instances. The use of such 360° radiation can be carried out using the instant system, which technique would avoid the occurrence of hot spots, i.e. localized areas of high dosage radiation, and indeed is often the desired technique.

Still there is an advante in non-uniform radiation distribution. If it is employed, for example, the avoidance of radiation in contact with some of the more sensitive parts of the body, eye lens, genitals, etc. is possible.

It is further seen that a technique that can be practiced with this system is off-center radiation. In such a technique, the part to be imaged is placed off-center, and radiation is applied during a part of the 360° swing, thereby resulting in even shorter exposure times.

The disclosure above has indicated that both two and three dimensional informational images can be made. While there is some overlap in the two terms, as known to the art, the distinctions are readily recognized. Thus, both types of images are obtainable herein.

There has thus been disclosed apparatus and a method for obtaining a two or three dimensional image of an object by X-ray scanning. The X-ray photons are transformed into light photons and impinge upon an image sensor such as a charge coupled device. This has the advantage that all of the information contained in the fan-like X-ray beam can be simultaneously converted into analog signals which are subsequently processed. Due to the combination of a wide fan-like X-ray beam with an area image detector, it is feasible to scan an object such as a patient in two seconds or less.

The image detectors employed herein, namely charge coupled devices, have the advantage of relatively low cost combined with high sensitivity and great geometrical accuracy. They are monolithic, thereby giving rise to relatively easy calibration, especially when a large plurality of them are used together. Easy calibration reduces down time of the machine.

Since there is almost no space between adjacent sensitive areas, ie. of adjacent CCDs, there is very little waste of information compared to other detection systems which may employ other types of detectors.

A further advantage toward achieving excellent imaging is the inherent excellent dynamic range of the CCDs now available.

Since certain changes may be made in the above apparatus and method without departing from the scope of the invention herein involved, it is intended that all matter contained in the above description and shown in the accompanying drawings shall be interpreted as illustrative and not in a limiting sense.

I claim:

1. A tomographic apparatus for examining a body by means of radiation such as x-ray or gamma radiation comprising:
(a) a body supporting structure for positioning a body relative to a rotatable source of radiation and relative to a detector,
(b) a source of penetrating radiation rotatable with respect to said body supporting structure and positioned on one side thereof,
(c) a radiation detector system located on the opposite side of said body supporting structure, rotatable or fixed, with respect thereto but fixed relative to said radiation source, which detection system comprises:
  (I) means for receiving and converting radiation received from said radiation source into light photons, wherein said means for receiving and converting radiation is a fluoroscopic screen, or is a scintillation crystal, and said screen or crystal is inclined at an angle with respect to the axis of the beam generated by said source, thereby yielding a greater light photon output,
  (II) an optical lens system aligned with said radiation converting means for focusing the light photons passing therethrough onto at least one charge coupled device.
  (III) at least one electronic charge coupled semiconductor device for receiving light photons and generating analog electric signals in response to the light photons received;
(d) an analog-to-digital converter for converting the analog signals generated by said semiconductor device into digital signals,
(e) means for processing said digital signals and means for reconverting said processed digital signals into an analog signal and displaying the thus obtained information, and
(f) means for rotating said radiation source and said radiation receiving means relative to said body supporting structure but fixed relative to each other.

2. The apparatus of claim 1 further including an averaging circuit interposed between the at least one charge coupled device and said A to D converter to permit less signal sampling for information processing.

3. The apparatus of claim 1 wherein a slit is interposed between said radiation source and the body to be scanned to cause a fan beam of radiation to impinge upon said body.

4. The apparatus of claim 3 wherein means is provided for moving the body to be scanned in a direction normal to that of the beam from said radiation source.

5. The apparatus of claim 1 wherein said lens system includes a cylindrical lens and a spherical lens.

6. The apparatus of claim 1 including:
(g) an angle detector comprising a means for detecting the relative location of the radiation source with respect to the body to be scanned and for advising the processing and displaying means about said location.

7. A tomographic apparatus for examining a body by means of radiation such as x-ray or gamma radiation comprising:
(a) a body supporting structure for positioning a body relative to a rotatable source of radiation and relative to a detector,
(b) a source of penetrating radiation rotatable with respect to said body supporting structure and positioned on one side thereof,
(c) a radiation detector system located on the opposite side of said body supporting structure, rotatable with respect thereto but fixed relative to said radiation source, which detector system comprises:
  (I) means for receiving and converting radiation received from said radiation source into light photons,
  (II) a plurality of optical lens systems aligned with said radiation converting means for focusing the light photons passing therethrough onto a plurality of charge coupled devices, one lens system per charge coupled device,
  (III) a plurality of electronic charge coupled semiconductor devices for receiving light photons and generating analog electric signals in response to the light photons received, (d) an analog-to-digital converter for converting the analog signals generated by said semiconductor device into digital signals, (e) means for reconverting said digital signals into an analog signal, means for processing said digital signals and displaying the thus obtained information, and (f) means for rotating said radiation source and said radiation receiving means relative to said body supporting structure but fixed relative to each other.

8. The apparatus of claim 7 including:

(g) an angle detector comprising a means for detecting the relative location of the radiation source with respect to the body to be scanned and for advising the processing and displaying means about said location.

9. The apparatus of claim 7 including means for advising the means for processing of the relative location of the radiation source with respect to the body to be scanned during the period of radiation.

10. A tomographic apparatus for examining a body by means of radiation such as x-ray or gamma radiation comprising:

(a) a body supporting structure for positioning a body relative to a rotatable source of radiation and relative to a detector, (b) a source of penetrating radiation rotatable with respect to said body supporting structure and positioned on one side thereof, (c) a radiation detector system located on the opposite side of said body supporting structure, rotatable with respect thereto but fixed relative to said radiation source, which receiving means comprises:

(I) means for receiving and converting radiation received from said radiation source into light photons, (II) a plurality of optical lens systems aligned with said radiation coverting means for focusing the light photons passing therethrough onto a plurality of electronic charge coupled devices, one lens system per charge coupled device, (III) at least one electronic charge coupled semiconductor device for receiving light photons and generating analog electric signals in response to the light photons received;

(d) means for processing and displaying the obtained information from said electronic charge coupled device, and (e) means for rotating said radiation source and said radiation receiving means relative to said body supporting structure but fixed relative to each other.

11. The apparatus of claim 10 wherein the means for processing and displaying includes a data organizer to sequence the data received from the plurality of charge coupled devices.

12. The apparatus of claim 11 further including an angle detector comprising a means for detecting the relative location of the radiation source with respect to the body to be scanned and for advising the processing and displaying means about said location.

13. The apparatus of claim 12 wherein a slit is interposed between said radiation source and the body to be scanned to cause a fan beam of radiation to impinge upon said body.

14. The apparatus of claim 12 further including an averaging circuit interposed between the charge coupled devices and said means for processing and displaying to permit less signal sampling for information processing.

15. The apparatus of claim 10 including means for advising the means for processing of the relative location of the radiation source with respect to the body to be scanned during the period of radiation.

* * * * *

UNITED STATES PATENT AND TRADEMARK OFFICE
CERTIFICATE OF CORRECTION

PATENT NO. : 4,298,800
DATED : November 3, 1981
INVENTOR(S) : Arnold Goldman

It is certified that error appears in the above—identified patent and that said Letters Patent is hereby corrected as shown below:

Delete columns 11 and 12 appearing on the reverse side of columns 5 and 6 and substitute the attached columns 7 and 8 therefor.

Column 15, line 8, "advante" should read -- advantage --.

Signed and Sealed this

Second Day of March 1982

[SEAL]

Attest:

GERALD J. MOSSINGHOFF

Attesting Officer

Commissioner of Patents and Trademarks like beam 15 is now directed toward an object 12. As explained before, this may be some inanimate object such, for example, as a core which has been drilled for oil exploration purposes. Alternatively, it may be a part of a patient such, for example, as a patient's brain or kidneys.

The X-ray beam 15 having passed through the object 12 now impinges upon a detector system comprising a fluoroscopic medium that is either directly coupled to an optically sensitive charge coupled device. Alternatively, there may be interposed a converging lens or lens-mirror system to accept the visible image from the fluoroscopic screen and deliver it to the CCD. This fluoroscopic medium may be either a fluoroscopic screen or a scintillation crystal 14. As is known in the art, the fluoroscopic screen does not intensify the X-ray signal. The fluoroscope merely changes the X-ray signal to a light signal.

Preferably, as clearly shown in Fig. 2, the screen is tilted with respect to the axis of the X-ray beam 15. The purpose of this tilt is to be able to absorb more of the X-ray photons which are then converted by the screen into light photons. The tilt also removes the detector from the path of the X-rays. If a scintillation crystal is used in place of the screen, the need for tilting is decreased. A suitable scintillation crystal would be cesium iodide doped with thallium. However, crystals are more expensive than screens in today's market, are less efficient in conversion to light and often present a less desirable spectrum to the charge coupled device. Fortunately research is making progress in the area. As will be subsequently explained, due to the fact that each X-ray photon has a high energy, it is capable of generating a plurality of light photons. However, it should be realized that all the information is contained only in the X-ray photons. Hence, if a number of light photons are generated by a single X-ray photon, they will all carry the same information.

The fluoroscopic screen 14 may, for example, consist of gadolinium oxysulfide (Eu). Such a screen has a high absorption for the X-rays and a high efficiency of conversion of the X-rays to light photons. It is also feasible to utilize a zinc cadmiumsulfide screen which is even more efficient in conversion. However, this last screen has a lower X-ray absorption and generates green light, whereas it is desired to have red light because of the response characteristics of the charge coupled devices currently available, as is explained below.

As indicated before, the screen 14 should be tilted with respect to the axis of the beam and the angle may be on the order of 60° to increase the absorption of the X-rays. Tilting the screen 14 increases the number of light photons generated by increasing the path length and therefore the number of X-ray photons absorbed. Of course there are other factors to consider to determine the number of light photons, e.g. absorption coefficient of the screen material.

The thus obtained light photons are now made to impinge on a charge coupled area image device 16. The nature of such devices is generally known and are available in the marketplace from Fairchild semiconductor. A typically useful one is CCD-121. It is believed that there are many significant advantages to be obtained in employing a CCD in a tomographic system. These low noise devices can detect a light signal from a fluoroscope, which signal has not been amplified. Since there is no intervening amplification, detection is very accurate both in terms of signal strength and signal location, i.e. where it is in space. The CCD acts as a detector and not as an amplifier. An amplifier amplifies or strengthens a signal; a CCD does not.

This electro-optical device detects a light signal and creates electron pairs which are transmitted along the chip to a pre-amplifier which is usually a part of the same chip in which lies the CCD. The analog signal (electrical) is then in a separate unit, amplified an adequate amount for it to be able to be fed to an A-D converter. Thus, on the chip, at most, there is some pre-amplification. As will be explained in more detail further on, the data once converted to an optical format is utilized with a reconstruction algorithm. To repeat again, an area image device of the charge coupled type has the advantage of great sensitivity and efficiency coupled with extreme geometric accuracy. That is, the analog signal which is created by the device 16 depends upon the precise area where the light photons impinge. On the other hand, since there is no intensification of the light image, there is going to be some loss in terms of the information received i.e. quanta photons available to be operated upon by the CCD. However, an adequate amount is present such as not to require increased radiation dosages.

Preferably, although not necessarily, a lens system 20 is used for imaging the screen 14 upon the device 16. This lens system may consist of a spherical lens 21 and a cylindrical lens 22. The purpose of the cylindrical lens is to reduce the width of the light beam because the sensitive area of the charge coupled device 16 has a ratio of length to width greater than the X-ray fan beam impinging on the screen 14. The cylindrical lens may, for example, consist of a glass rod having a diameter of between 2 and 4 millimeters. The spherical lens 21 should be a large aperture lens having an f of approximately 0.7, where f is the ratio of the diameter of the lens to the focal length. This may conveniently be a Fresnel lens e.g. of the type manufactured by Ealing under No. 24-0010 or 24-0044. This is a positive aspheric lens. It is also to be understood that tapered fiber optics devices can be used to concentrate the light to be received by CCD elements. Mention may be made of tapered fiber optical systems made by American Optical, Stockbridge, MA on order to specification for such purposes.

It will be realized by inspection of FIG. 2 that the lenses 21 and 22 are parallel to the plane of the fluoroscopic screen 14 and normal to the axis 24.

The device 16 combines low cost with great accuracy in measuring the light. It also provides rapid cycling. That is, the information in the form of charge carriers in the respective potential wells can be rapidly read out by the application of suitable potentials. In addition, such devices have a broad dynamic range even at room temperature, although it is preferred to operate them at 0° C. or lower. As stated before, the Fairchild CCD Models 101 and 110 are suitable, although the CCD Model 121 is preferred.

It should be noted that the device 16 is primarily sensitive in the red or infrared spectral region. One reason why a fluoroscopic screen 14 is preferred which emits red or infrared light is that the number of electron hold pairs generated in response to the light photons falling on the sensor elements of the CCD, said number being designated K, is a function of light intensity and wavelength of the incident light and the elements of the CCD are most receptive to red usually. Thus, red light